(12) United States Patent
Freilich et al.

(10) Patent No.: US 8,986,381 B2
(45) Date of Patent: *Mar. 24, 2015

(54) STRUCTURAL/BIOLOGICAL IMPLANT SYSTEM (75) Inventors: Martin Allen Freilich, West Hartford, CT (US); John Robert Kelly, West Hartford, CT (US); Rebecca Lee Cochrane, Suffield, CT (US)

(73) Assignee: University of Connecticut, Farmington, CT (US)

( * ) Notice: Subject to any disclaimer, the term of this patent is extended or adjusted under 35 U.S.C. 154(b) by 103 days.

This patent is subject to a terminal disclaimer.

(21) Appl. No.: 13/362,105

(22) Filed: Jan. 31, 2012

(65) Prior Publication Data
US 2012/0197397 A1 Aug. 2, 2012

Related U.S. Application Data (63) Continuation of application No. 12/259,608, filed on Oct. 28, 2008, now Pat. No. 8,152,848, which is a continuation of application No. 10/867,487, filed on Jun. 14, 2004, now abandoned.

(60) Provisional application No. 60/478,705, filed on Jun. 13, 2003.

(51) Int. Cl.
*A61F 2/28* (2006.01)
*A61C 8/00* (2006.01)
(Continued)

(52) U.S. Cl.
CPC .............. *A61B 17/68* (2013.01); *A61C 8/0006* (2013.01); *A61L 27/32* (2013.01); *A61L 27/54* (2013.01);
(Continued)

(58) Field of Classification Search
USPC .................... 623/16.11, 17.17, 23.75–23.76; 433/173–174
See application file for complete search history.

(56) References Cited

U.S. PATENT DOCUMENTS

| 4,531,915 A | 7/1985 | Tatum, Jr. |
| 4,531,916 A | 7/1985 | Scantlebury et al. |

(Continued)

FOREIGN PATENT DOCUMENTS

| DE | 4226465 | 2/1993 |
| DE | 94 00 537.0 | 4/1994 |

(Continued)

OTHER PUBLICATIONS

Schmid, et al., N.E, Supraplant®, a Novel Implant System Based on the Principle of Guided Bone Generation, 2:199-202, 1991.

(Continued)

*Primary Examiner* — Nicholas Woodall
(74) *Attorney, Agent, or Firm* — McCarter & English, LLP (57) ABSTRACT

A structural/biological implant and method of use. The implant being utilized as a single or multiple staged system that is designed to encourage new alveolar bone growth with or without the need to obtain autologous bone. The implant has an apical portion that is fastened into existing bone, with the remainder of the implant left outside of existing bone. The exposed portion of the implant may have an external shape or configuration with a variety of attached and/or integrally formed mechanical retention and stability elements. Osteotropic/angiotropic material may be associated with the implant to induce and or conduct new bone growth and possible vascularization, thus, rather than fitting the implant into the bone, the bone is grown integratively with the implant.

30 Claims, 8 Drawing Sheets (51) Int. Cl.
  *A61B 17/68* (2006.01)
  *A61C 8/02* (2006.01)
  *A61L 27/32* (2006.01)
  *A61L 27/54* (2006.01)
  *A61L 27/56* (2006.01)
  *A61L 27/58* (2006.01)
  *A61B 17/80* (2006.01)

(52) U.S. Cl.
  CPC ............... *A61L 27/56* (2013.01); *A61L 27/58* (2013.01); *A61B 17/80* (2013.01); *A61L 2300/252* (2013.01); *A61L 2300/258* (2013.01); *A61L 2300/412* (2013.01)
  USPC .......... 623/16.11; 433/173; 433/174

(56) References Cited

U.S. PATENT DOCUMENTS

| | | | |
|---|---|---|---|
| 4,682,951 A * | 7/1987 | Linkow | 433/173 |
| 4,846,683 A * | 7/1989 | Lazzara et al. | 433/173 |
| 4,872,840 A | 10/1989 | Bori | |
| 5,196,016 A | 3/1993 | Buser | |
| 5,372,503 A | 12/1994 | Elia | |
| 5,397,235 A | 3/1995 | Elia | |
| 5,456,601 A | 10/1995 | Sendax | |
| 5,511,565 A | 4/1996 | Syers | |
| 5,538,424 A | 7/1996 | Gelb | |
| 5,632,745 A | 5/1997 | Schwartz | |
| 5,674,725 A | 10/1997 | Beertsen et al. | |
| 5,759,033 A | 6/1998 | Elia | |
| 5,769,898 A | 6/1998 | Jisander | |
| 5,833,463 A | 11/1998 | Hurson | |
| 5,839,899 A | 11/1998 | Robinson | |
| 5,961,329 A | 10/1999 | Stucki-McCormick | |
| 5,976,140 A | 11/1999 | Haas | |
| 5,989,027 A | 11/1999 | Wagner et al. | |
| 6,227,858 B1 | 5/2001 | Lundgren | |
| 6,238,214 B1 | 5/2001 | Robinson | |
| 6,270,346 B1 | 8/2001 | Grabenhofer | |
| 6,394,807 B2 | 5/2002 | Robinson | |
| 6,547,564 B1 | 4/2003 | Hanson | |
| 6,616,698 B2 | 9/2003 | Scarborough | |
| 8,152,848 B2 | 4/2012 | Freilich et al. | |
| 2001/0012607 A1 | 8/2001 | Robinson | |
| 2003/0118968 A1 * | 6/2003 | Massoud | 433/173 |
| 2003/0232308 A1 | 12/2003 | Simmons | |
| 2006/0008773 A1 | 1/2006 | Liso | |

FOREIGN PATENT DOCUMENTS

| | | |
|---|---|---|
| EP | 00574091 | 12/1993 |
| JP | 03-505684 | 12/1991 |
| JP | 04-231042 | 8/1992 |
| JP | 04-341256 | 11/1992 |
| JP | 04-224141 | 8/2002 |
| WO | WO 90/07308 | 7/1990 |
| WO | WO 01/62180 | 8/2001 |
| WO | WO 02/19937 | 3/2002 |
| WO | WO 03/048347 | 6/2003 |
| WO | WO 2005/016388 | 2/2005 |

OTHER PUBLICATIONS

Renvert, et al, Supracrestal Bone Growth around Partially Inserted Titanium Implants in Dogs, Clinical Oral Implants Res 7: 360-365, 1996.
Huang, et al., Bone Morphogenetic Proteins and Osseointegration: Current Knowledge Future Possibilities, vol. 47, pp. 206-223, Ulf M.E., 2000.
Roos-Jansaker, et al.., "Dog Model for Study of Supracrestal Bone Apposition Around Partially Inserted Implants", *Clin Oral Implants Res* 13: 455-459, 2002.
Franke-Stenport, et al., Enamel Matrix Derivative and Titanium Implants, J. Clin. Periodontol 30: 359-363, 2003.
Franke-Stenport, et al. Failure to Induce Supracrestal Bone Growth Between and Around Partially Inserted Titanium Implants Using Bone Morphogenetic Protein (BMP): An Experimental Study in Dogs, Clin Oral Implants Res 14:219-225, 2003.
Wikesjo, et al., The Critical-Size Supraalveolar Peri-Implant Defect Model: Characteristics and Use, J. Clin Periodontol, 33: 846-854 2006.
Leknes, et al., Alveolar Ridge Augmentation Using Implants Coated With Recombinant Human Bone Morphogenetic Protein-2: Radiographic Observations, UlfM.E., pp. 1027-1033, 2008.
Wikesjo, IADR Symposium 1575, 2008.
Supplemental European Search Report dated Sep. 2, 2008.

\* cited by examiner

STRUCTURAL/BIOLOGICAL IMPLANT SYSTEM

CROSS REFERENCE TO RELATED APPLICATIONS

This application is a continuation of U.S application Ser. No. 12/259,608, filed Oct. 28, 2008, now U.S. Pat. No. 8,152, 848, which is a continuation of U.S. application Ser. No. 10/867,487, filed Jun. 14, 2004, now abandoned, which claims the benefit of U.S. Provisional Application No. 60/478,705, filed Jun. 13, 2003, the contents of which are incorporated by reference in their entireties.

STATEMENT REGARDING FEDERALLY SPONSORED RESEARCH OR DEVELOPMENT

This invention was made with Government support under Grant No. DE14187 awarded by the National Institute of Dental and Craniofacial Research. The Government has certain rights in the invention.

FIELD OF THE INVENTION

This invention relates generally to a structural/biological implant and method for encouraging bone growth with or without use of graft materials which may include autogenous bone, autologous or engineered cells, mineralized materials, demineralized bone matrix, alginates, collagen materials, and articles useful therein.

BACKGROUND OF INVENTION

Inadequate bone volume is a well recognized problem in the craniofacial and orthopedic fields. For example, ordinarily, a dental implant must be fit into an implant bed within existing bone and corresponding in shape to the implant. Standard implants have a cylindrical or slightly tapered shape in order to allow for a path of placement into bone with the close adaptation needed for stability and to encourage the selective re-population of the implant site with osteogenic potential cells versus being encapsulated within fibrous tissue. In a large proportion of clinical cases, there is inadequate bone height and/or width for the placement of standard endosseous dental implants.

Dental implants to replace missing teeth are 90-95% successful in clinical practice, when placed under optimal conditions. These conditions include good systemic health of the patient and acceptable bone quality, acceptable bone volume and acceptable bone shape at the implant site. Unfortunately, bone resorbs after tooth loss. Due to this continued bone loss, a substantial segment of the population has insufficient bone volume to benefit from implant placement. Bone grafting is currently the standard method for increasing the height and width of the bone ridge, and thereby maxillofacial bone volume. Current bone graft methods include painful, invasive and sometimes hazardous or prolonged procedures generally requiring an extensive donor site at locations such as the rib, hip or leg bone or blocks of bone from the jaw.

Tissue engineering methods to augment bone volume, in edentulous regions where standard implant placement is not possible, are under intense development. These methods involve the use of scaffolds, growth factors and cells with osteogenic potential. However, at present there are significant limitations to the dimensions (especially thickness) of material that can be implanted due to issues involving extra-cellular transport of metabolites and products; the lifetime and effective diffusion distance and presentation timing of signaling moieties; and the multitude of support functions provided by a properly distributed vasculature. Thus, for example, many tissue-engineered products are limited to thicknesses of two to three millimeters, likely an inadequate dimension to be clinically meaningful in one surgical step.

SUMMARY OF THE INVENTION

Briefly stated, the invention in a preferred form is a structural/biological implant and a method of use thereof for encouraging bone growth around the implant for structural purposes, with or without the use of autologous bone grafts, cells and/or therapeutic agent delivery. The invention in some forms may also be used with autologous bone grafts.

Another embodiment of the invention is a bone augmentation dental implant system used where existing jawbone levels are inadequate for the placement of standard dental implants.

Generally, a portion of the implant is fastened into existing bone, with the remainder of the implant extending outside of existing bone. The extending or exposed portion of the implant has an osteointegrative surface which may include an external shape or configuration including at least one of a variety of attached and/or integrally formed mechanical retention and stability elements. New bone growth occurs around the exposed portion of the implant thereby increasing bone height and volume in the patient.

Biologic materials which may be osteoinductive, osteoconductive, osteotropic and/or osteogenerative (herein referred to as osteotropic materials) may be used in conjunction with the implant to induce, promote, or enhance new bone growth around the exposed portion of the implant.

Vascular augmentation and/or enhancement may be achieved through use of angiogenic materials such as chemical agents, proteins and nucleic acids encoding growth factors herein referred to as angiotropic materials. These osteotropic/angiotropic materials include, but are not limited to, conductive and/or inductive scaffolds that support and direct regeneration of bone or vascular endothelium and often may additionally incorporate, growth factors, and progenitor cells. The osteotropic/angiotropic material provides an immediately available surface for bone cell adhesion and growth. Further, these materials may be paired with appropriate osteoinductive factors to provide environmental conditions that advance osteogenesis.

Thus, rather than fitting the implant into existing bone volume, new bone volume and supporting vasculature, is grown into and around exposed portions of the implant providing a positionally stable and biologically integrated implant. Consistent positional retention and stabilization of the osteotropic/angiotropic material by the implant structure can also be achieved through the close adaptation of the osteotropic/angiotropic material to the implant structure. The implant is amenable to use with tissue engineering techniques. For example, this includes the transplantation of undifferentiated stem cells, progenitor cells for bone or cartilage, or differentiated cells into scaffold materials. This may also include transfection vector therapy to induce growth factor expression from local cells or cells sequestered into or transplanted into scaffold materials at the site of the osseous deficiency.

The invention allows implants to be used in locations where bone height and/or bone shape is not adequate for existing implant systems. For example, conventional implants typically require ten to twelve millimeters of bone height. However, only four to six millimeters of height are required by the inventive implant at the beginning of treatment. During treatment an additional two to six millimeters of bone can be grown around the implant in one or more surgical procedures.

Portions of the implant can be made from resorbable or non-resorbable materials, and can be shaped or configured to optimally achieve positional stability since bone is grown integrally with the implant. The resorbable and/or non-resorbable endosseous dental implant may also be utilized with tissue engineered materials used with reduced bone levels and/or to enable segmental osteogenesis.

In general, the material of the invention may be alternately formulated to comprise, consist of, or consist essentially of, any appropriate components herein disclosed. The material of the invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

BRIEF DESCRIPTION OF THE DRAWINGS

Other objects and advantages of the invention will be evident to one of ordinary skill in the art from the following detailed description with reference to the accompanying drawings, in which.

DETAILED DESCRIPTION OF THE INVENTION

The implant in one embodiment of the invention as illustratively shown in FIG. 1 has a central axis (not shown) extending between a coronal end 10 and an apical end 12. The implant includes a level I assembly 10 having an initial implant portion 16 with an anchor portion 18. The anchor portion 18 may be substantially axially symmetric to the central axis. The anchor portion 18 has an exterior surface. In one embodiment the anchor portion 18 exterior surface has fastening means such as screw threads 20 helically disposed thereon. The threads advantageously have a minimal spacing, for example, less than 1 mm, and are self-tapping for optimal engagement and adaptation to existing alveolar bone. Other fastening means may be disposed on the anchor portion 18 exterior surface to help secure the anchor portion 18 to existing bone. The anchor portion 18 may for example be between about 3 mm and about 6 mm in length. The initial implant portion 16 may also have a transmucosal portion 22 being about 2 mm in length. The transmucosal portion 22 may be integrally formed with the initial implant portion 16 or may be a discrete part separable from the initial implant portion 16.

The transmucosal portion 22 may, as illustratively shown in FIG. 1, have a connecting surface such as a threaded bore 26. The walls of the bore may define a slot 28 or other tool engagement surface well known in the art.

Figures 6A, 6B:
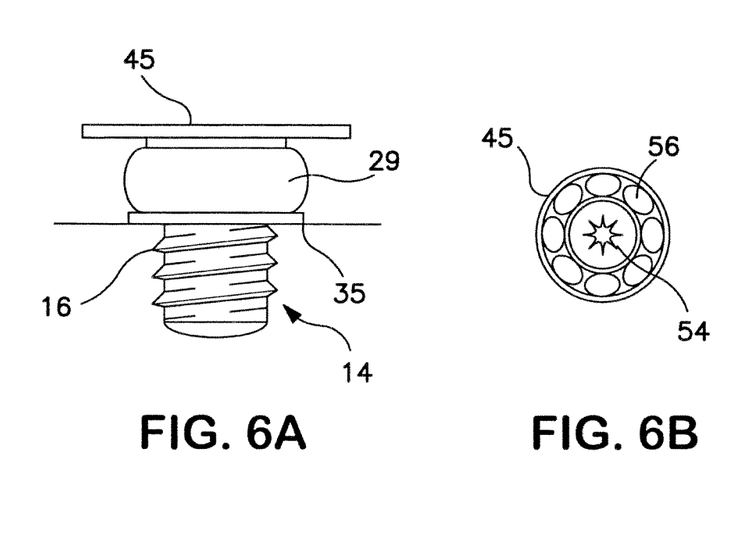
FIG. 6A is a side view of an embodiment of the inventive assembled stage I implant.
FIG. 6B is a top view of the inventive embodiment 6A.
Figure 6C:
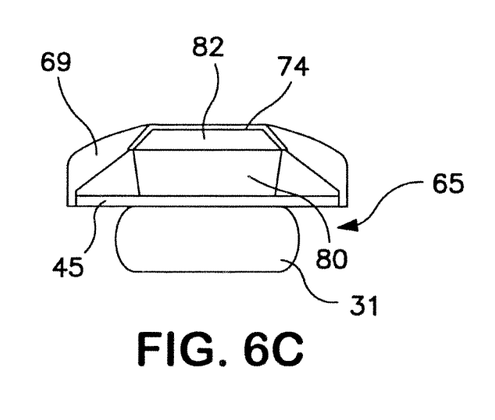
FIG. 6C is a side view of a portion of an embodiment of the inventive assembled stage II implant.
Figure 6D:
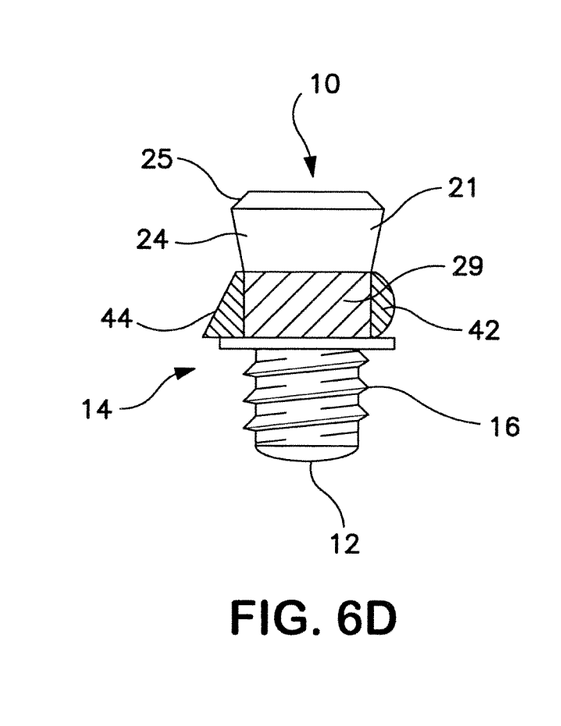
FIG. 6D is a side view of an embodiment of the inventive stage I assembly implant.
Figure 6E:
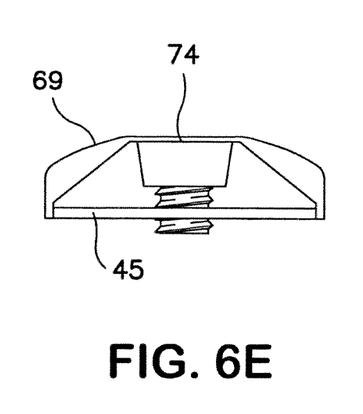
FIG. 6E is a side view of a portion of an embodiment of the inventive assembled stage II implant.

In another embodiment of the invention illustratively shown in FIG. 6D, the transmucosal portion of the initial implant portion 16 may have a polished collar 24. The polished collar may be approximately 2 mm in axial length, terminating with a finish line 25. The finish line 25 may be, for instance, angled relative to the central axis extending between the coronal end 10 and the apical end 12.

In some embodiments it is desirable to have a separate transmucosal portion. For example, when multiple stages are to be employed, the initial structural implant has a separate transmucosal portion (not shown) and may or may not include the polished collar.

The transmucosal portion need not be axially symmetric to the central axis. In some embodiments of the invention (not shown) the transmucosal portion may have a cross-sectional shape designed to provide esthetic, biologic or further mechanical advantages. Such asymmetric shape may, for instance, be in a tooth root form, which would provide esthetic value, or mechanical stability of a prosthetic feature.

An osteointegrative portion 30 of the implant is disposed apical to the transmucosal portion 22. The transmucosal portion 22 and the osteointegrative portion 30 may be configured and/or adapted to aid in the installation and positioning of osteotropic/angiotropic material 32. For example, the transmucosal 22 and osteointegrative 32 portions may have a shape which is complementary to an opening in the osteotropic/angiotropic material 32 to aid in the alignment and passage of the osteotropic/angiotropic material 32 over the transmucosal portion 22 and the osteointegrative portion 30.

With reference to FIG. 1, the initial implant portion 16 has an osteointegrative portion 30, which, for example, is about 2 mm in length. The dimension and position of the osteointegrative portion 30 should be understood to be variable depending on osteointegrative potential of the site. The osteointegrative potential may vary depending on, for example, the type(s) of osteotropic/angiotropic material 32 associated with the implant and the location, morphology and physiology of the implant site. The osteointegrative portion 30 is typically located between the transmucosal portion 22 and the anchor portion 18. However, the osteointegrative portion 30 may be located in other locations. For example, the osteointegrative portion 30 may be located at the apical end 12 of the initial insert portion 16. It should also be understood that there may be a plurality of osteointegrative portions present on the implant (not shown).

The osteointegrative portion in any of the embodiments may have, for example, a surface which is bioactive and designed to promote rapid osteointegration or closely adapted new bone growth while being configured to achieve increased stability and retention to the newly grown bone. Bioactivity of the surface may be achieved through, for example, modifying the chemical surface properties of the osteointegrative portion. For example, calcium phosphate may be used to coat the surface of the osteointegrative portion.

The external shape of osteointegrative portion 30 does not need to be axially symmetric relative to the central axis. The osteointegrative portion 30 may, for example, have any number of projections, undulations, cavities, etchings, and/or other such features designed to resist axial tipping, or torsional loads and/or provide enhanced osteointegration. The osteointegrative portion 30 can be shaped or configured in part to achieve increased retention and stability characteristics for a given osteointegrative portion 30 length. For example, the use of a reverse taper shape (not shown) in which the osteointegrative portion increases in diameter from the coronal end 10 toward the apical end 12 operates to wedge the implant within the newly formed bone. The osteointegrative portion 30 may also have protrusions (not shown) which operate to stabilize the implant as bone forms around the protrusions.

Figure 5A:
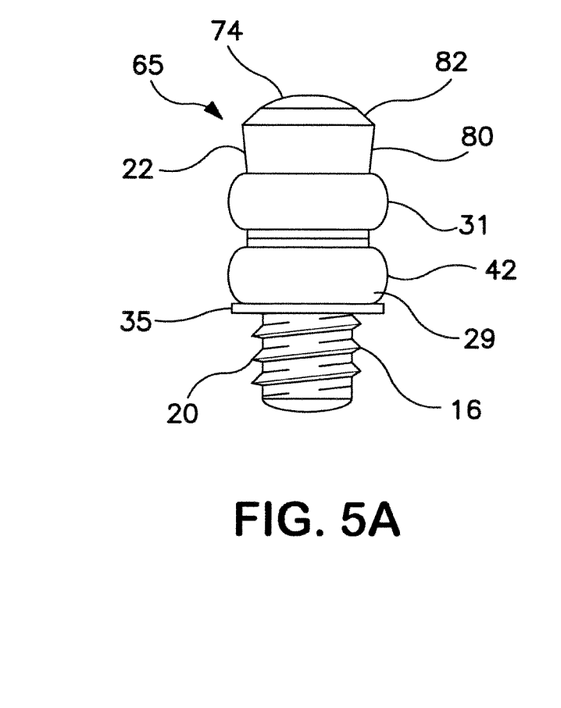
FIGS. 5A-5C are side views illustrating examples of one embodiment of the inventive staged implant consistent with the present invention.

The osteointegrative portion 29 may be configured in whole or part to increase positional stability of the implant by providing mechanical support as bone grows around the configured area. For example the osteointegrative portion 29 may have an ovate shape 42 as shown in FIG. 5A or an undercut shape 44 as shown in FIG. 5D.

The osteointegrative portion may also incorporate a resorbable or a non-resorbable porous surface capable of uptake and sustained release of endogenous or exogenous macromolecules associated with the differentiation and proliferation of precursor cells to become osteoblasts and stimulate osseous formation. For example, this surface may be used as a carrier for drugs, proteins or genetic material. In one embodiment of the invention, this surface of the osteointegrative portion may carry drugs or biomolecules that elicit endochondral bone formation as a prelude to cortical bone formation directly adjacent to the implant site.

An extender 34 may also be present that removably attaches to the coronal end 10. The extender may, for example, have threads disposed to allow engagement with the threaded bore 26. The attached extender 34 axially extends in the coronal direction to allow osteotropic/angiotropic material 32 to be engaged with the extender 34. This engagement allows precise and controlled positioning of the osteotropic/angiotropic material 32 over the transmucosal portion 22 and osteointegrative portion 30 in a surgical environment.

A preliminary stabilizer 36 may be present which extends laterally outwardly from the outermost surface of the anchor portion 18. For example, the preliminary stabilizer 36 may extend outwardly about 2 mm. The preliminary stabilizer comes into contact with, for example, a countersunk area in the prepared bone surrounding the embedded anchor portion 18. The preliminary stabilizer 36 may act to provide lateral stability to the implant as well as retentive stability after formation of new bone around the preliminary stabilizer 36.

In one embodiment of the invention, the preliminary stabilizer 36 is a separable part that may not be present when the anchor portion 18 is embedded to a sufficient depth in bone, for example to about 4 mm to about 6 mm. In this embodiment the preliminary stabilizer 36 has a central opening 38 which may be internally threaded. The central opening 38 may be threaded onto the portion of the initial implant, which, for example, extends above the bone. The preliminary stabilizer 36 may be secured against the bone by a preliminary stabilizer nut 40.

In another embodiment of the invention, illustratively shown in FIGS. 5A, and 6A, the preliminary stabilizer 35 is an integral part of the initial insert portion 16. In this embodiment the preliminary stabilizer 35 is permanently attached to, or formed with, the initial insert portion 16. The preliminary stabilizer 35, in use, comes into contact with the bone as the implant embeds.

The preliminary stabilizer may also be fixed to the implant in a manner that allows rotation of the preliminary stabilizer about the initial implant portion 16. For example, there may be a circumferential groove (not shown) formed in the initial implant portion 16 into which a lip (not shown) of the preliminary stabilizer 35 engages, such that the preliminary stabilizer 35 is fixed axially but can rotate about the initial implant portion 16.

Figure 8A:
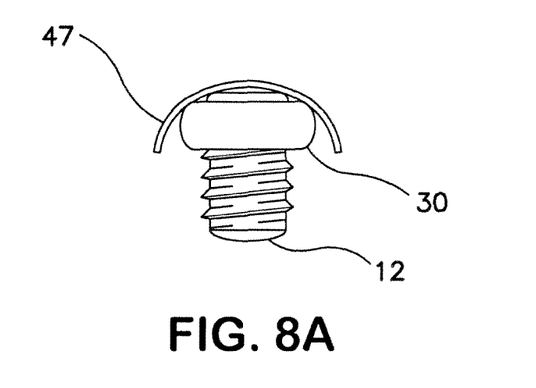
FIG. 8A is a side view of one embodiment of an inventive staged implant.
Figure 8B:
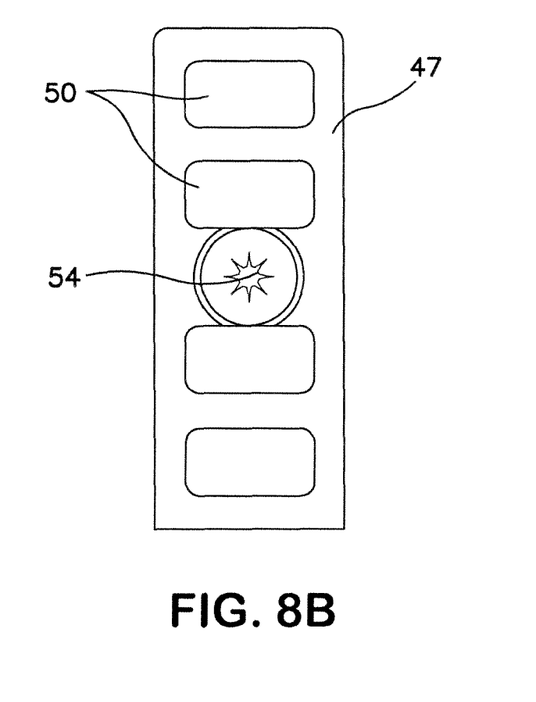
FIG. 8B is a top view of the inventive staged implant of FIG. 8A.

In one embodiment of the invention, a second stabilizer, termed an osteotropic/angiotropic material stabilizer 46, shown in FIG. 1, may be attached to the structural implant. In other embodiments the osteotropic/angiotropic material stabilizer 47, as illustratively shown in FIGS. 8A and 8B may have a curved or arcuate planar form having one or more cutouts 50 and/or protrusions (not shown). These cutouts 50 provide enhanced stabilization, cell population, and/or vascularization of the biologic material. The osteotropic/angiotropic material stabilizer 46 may have a threaded opening 52, illustratively shown in FIG. 1, to engage, for example, threads on initial implant portion 16.

Figure 2A:
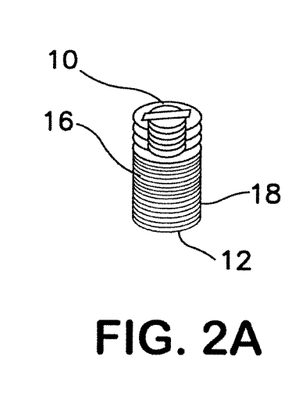
FIGS. 2A-2G are perspective views illustrating examples of some inventive embodiments of stage I and stage II implant system assemblies.
Figure 2B:
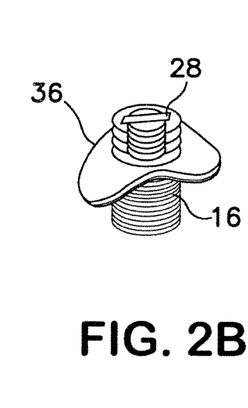
Figure 2C:
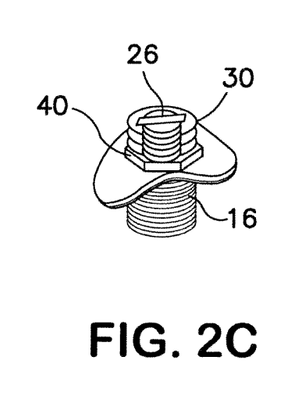
Figure 2D:
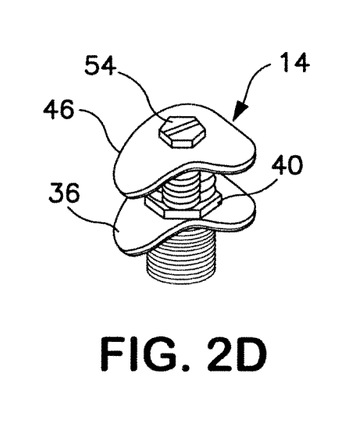
Figure 2E:
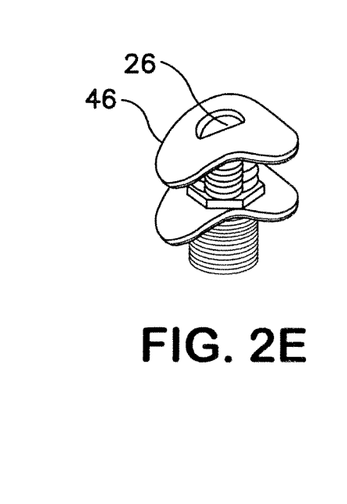

The osteotropic/angiotropic material stabilizer 46 may be positioned on the coronal end 10 of the initial implant portion 16, as illustratively shown in FIG. 2D, and be secured in place with a stage I cover screw 54 that engages with a connecting surface such as bore 26. Alternatively, the osteotropic/angiotropic material stabilizer may be formed integral with the cover screw (not shown) such that the stabilizer extends laterally outwardly from a portion of the cover screw. For example, the head of the cover screw may have a portion that extends radially outwardly about a central axis.

In any embodiment the osteotropic/angiotropic material stabilizer may be formed of any suitable material known in the implant arts, including resorbable organic and/or inorganic materials, or non-resorbable materials such as metal and ceramic.

As shown in FIG. 1 the osteotropic/angiotropic material stabilizer 46 may be disposed with osteotropic/angiotropic material 32 on the initial implant portion 16 in order to further prevent any potential movement of the osteotropic/angiotropic material 32. The osteotropic/angiotropic material 32 is prevented from moving by, for example, the osteotropic/angiotropic material stabilizer 46 exerting pressure on the osteotropic/angiotropic material 32 such that the osteotropic/angiotropic material 32 is held against the preliminary stabilizer 36 and/or the bone. In one embodiment of the invention, illustratively shown in FIG. 6B, the osteotropic/angiotropic material stabilizer 45 has a plurality of openings, each 56. The openings 56 allow vascular in-growth to the area of bone growth to occur therethrough. The openings 56 may also aid in retaining the osteotropic/angiotropic material by, for example, allowing portions of the osteotropic/angiotropic material to protrude into the openings 56 when the osteotropic/angiotropic material stabilizer 45 exerts pressure on the osteotropic/angiotropic material.

Figures 3A, 3B, 3C:
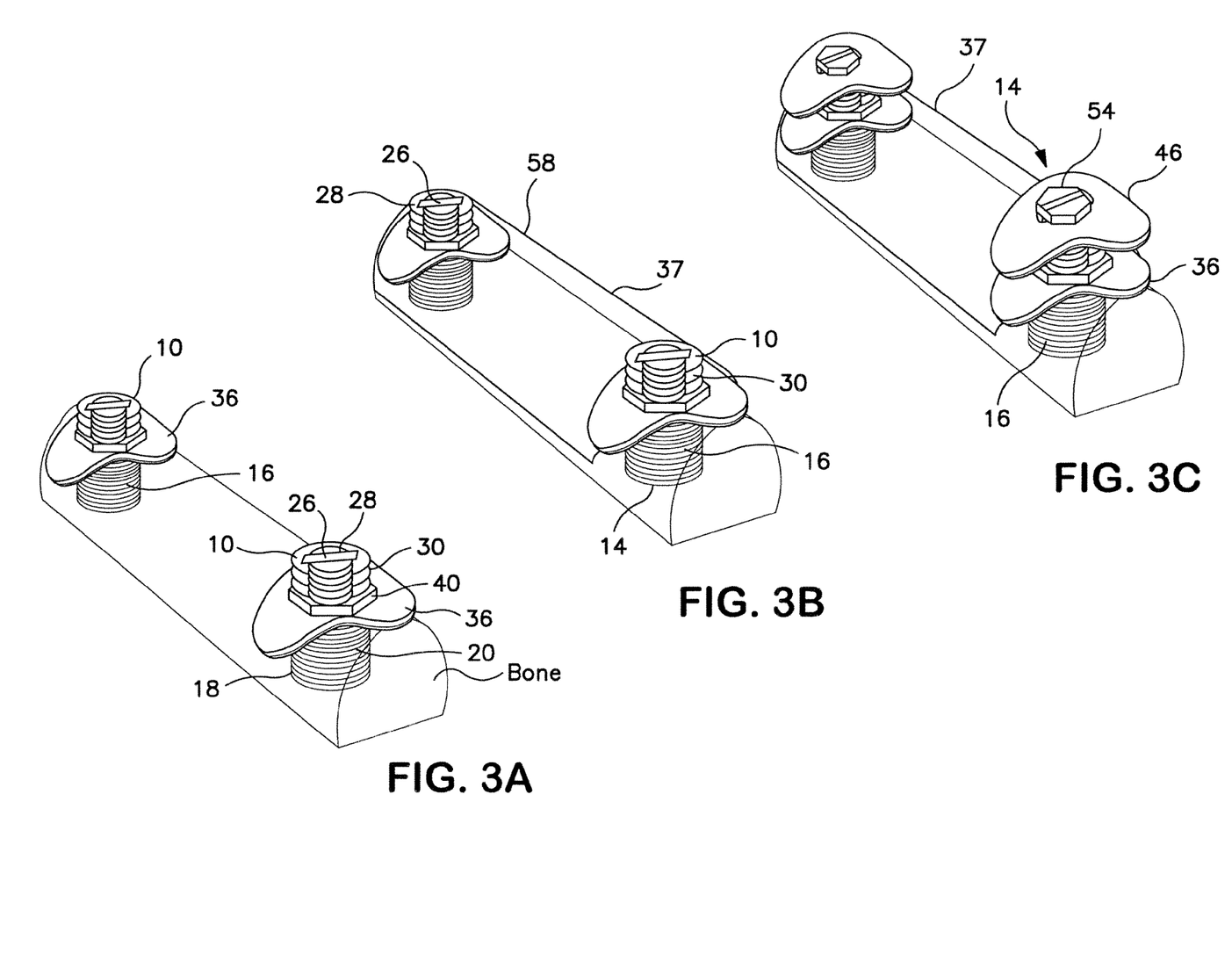
FIGS. 3A-3C are perspective views illustrating examples of some inventive staged implants with osteotropic/angiogenic materials embedded in bone during a stage I surgery process.

With reference to FIG. 3C, the osteotropic/angiotropic material stabilizer 46 and/or osteotropic/angiotropic material 37 may also support the mucoperiosteal flaps present around the implant site (not shown). The mucoperiosteal flaps can be used to cover the implants at the conclusion of the surgical procedure placing the implant. In the event that insufficient tissue is present due to the volume occupied by the implant periosteal releasing incisions; a split flap or a soft tissue graft may be used to cover the implant.

Osteotropic/angiotropic material in any of the embodiments may comprise those materials known as scaffold matrices made from a variety of materials well known in the medical art. Examples of such materials include autogenous bone, bone allograft, synthetic polymers, natural polymers, ceramics, and/or composite materials. These materials generally provide surfaces and conduits which are utilized by osteoblast lineage cells and osteoblasts. In addition, the osteotropic/angiotropic material may allow for such things as retention, stabilization, controlled release, and/or other bioavailability modulation of osteoactive compounds and/or products. For example, the osteotropic/angiotropic material may include resorbable collagen sponges soaked with recombinant human bone morphogenetic protein (rhBMP) and/or VEGF (for vascular potentiation) which may be either covered or uncovered with a non-resorbable barrier membrane 58, as show in FIG. 3B. The membrane 58 may act, among other things, as a barrier to the in-growth of epithelial cells and connective tissue fibroblasts. Suitable barrier membrane 58 materials include polytetrafluoroethylene and collagen. It should be understood that the osteotropic/angiotropic material may also have the form and rigidity to aid in stabilization of the implants. For example, the use of osteotropic/angiotropic materials such as polymers, ceramics, composites, cements, autogenous bone, bone allograft, or other rigid material, may add mechanical support to the implants.

Figure 7A:
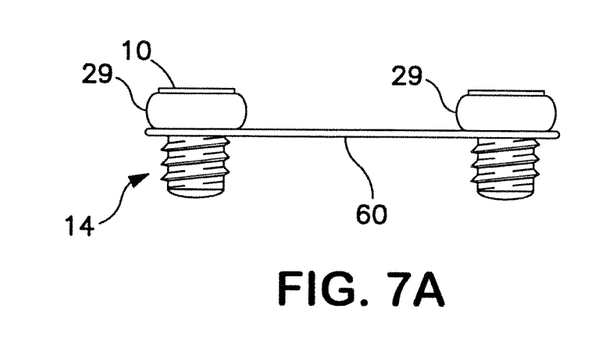
FIG. 7A is a side view of inventive trans-implant elements used with two stage I implants.
Figure 7B:
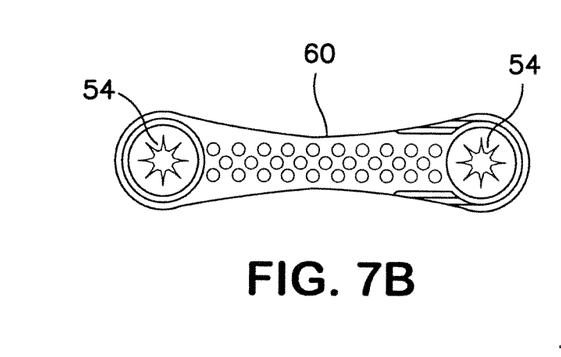
FIG. 7B is a top view of the inventive element of FIG. 7A.
Figures 7C, 7D:
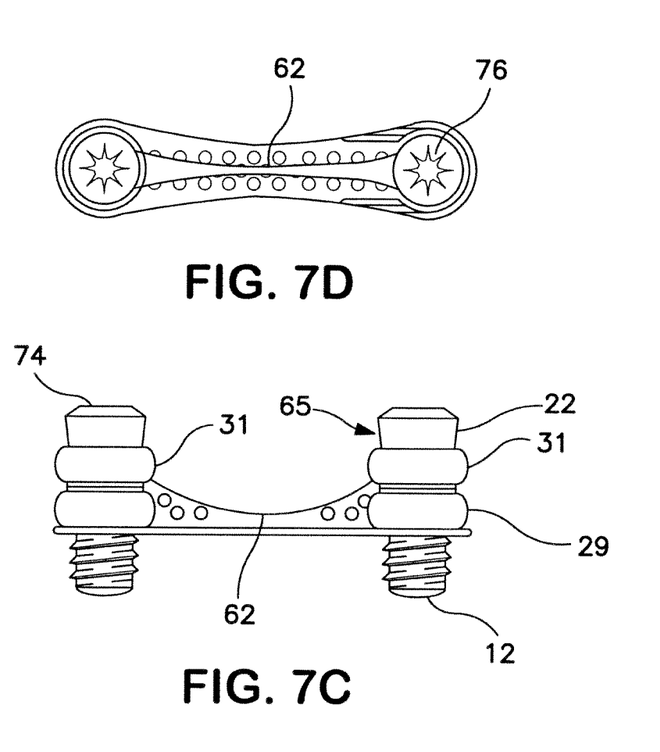
FIG. 7C is a side view of inventive trans-implant elements used with two stage II implants.
FIG. 7D is a top view of the inventive element of FIG. 7C.

The initial implant portion 16, as shown in FIG. 3B, may be used alone or as part of a plurality of adjacent implants, and may incorporate, secure, and/or stabilize such things as the osteotropic/angiotropic material 37. As illustratively shown in FIGS. 7A-7D, stabilization may be aided by trans-implant elements such as mesh 60, or plate 62. The trans-implant elements such as mesh 60 and plate 62 may provide mechanical stability to the implants. In addition, osteotropic/angiotropic material (not shown in FIG. 7) may be associated with the mesh 60 and/or plate 62 such that the trans-implant elements provide stability and retention of the osteotropic/angiotropic material through mechanical interaction to the osteotropic/angiotropic material.

As illustratively shown in FIG. 2D, an osteotropic/angiotropic stabilizer cover screw 54 may be fixed to the implant through engagement of the cover screw threads with the threaded bore 26 of the initial insert 16 to form a stage I assembly 14.

Figure 2F:
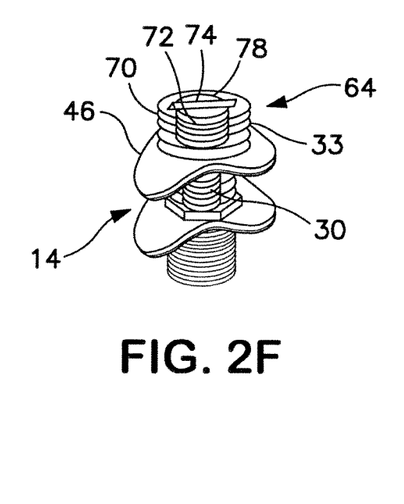
Figure 2G:
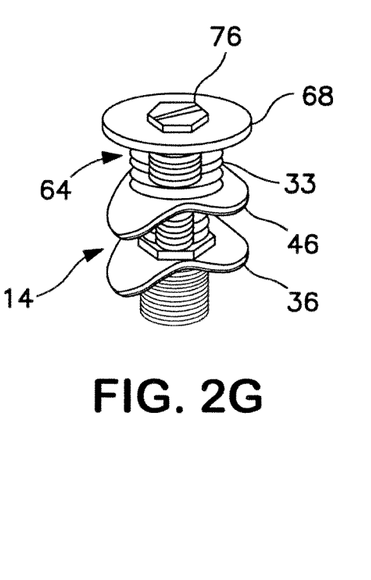

In one embodiment of the invention, shown in FIG. 2G, a stage II assembly 64 may be utilized if, for example, additional bone growth over that available from a stage I assembly is required. It should be understood that more than one additional stage assembly may be utilized if additional bone growth is required. The stage II assembly 64 replaces the cover screw 54 as illustrated in FIGS. 2F and 2G.

Figure 1A:
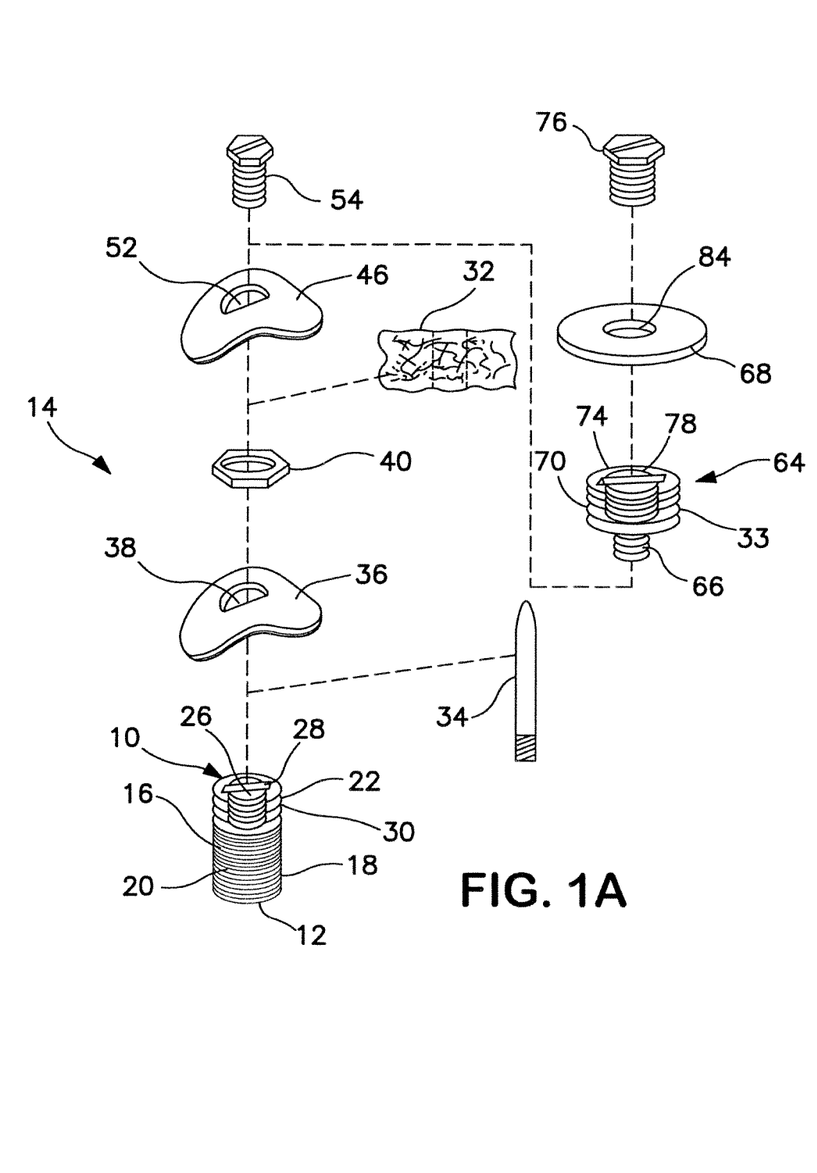
FIG. 1A is an exploded view illustrating various components of one embodiment of the inventive staged implant system.

The stage II assembly 64, as shown in FIG. 1A, includes an engagement portion 66, and a body portion 70. The stage II assembly 64 also includes an osteointegrative portion 33 which may, as previously discussed, be a resorbable or non-resorbable porous surface material capable of, for example, uptake, release, and sustained release of endogenous or exogenous macromolecules, such as drugs, proteins and genetic material, associated with the differentiation and proliferation of vascular cells or precursor cells to become osteoblasts and stimulate osseous formation.

Figures 5B, 5C:
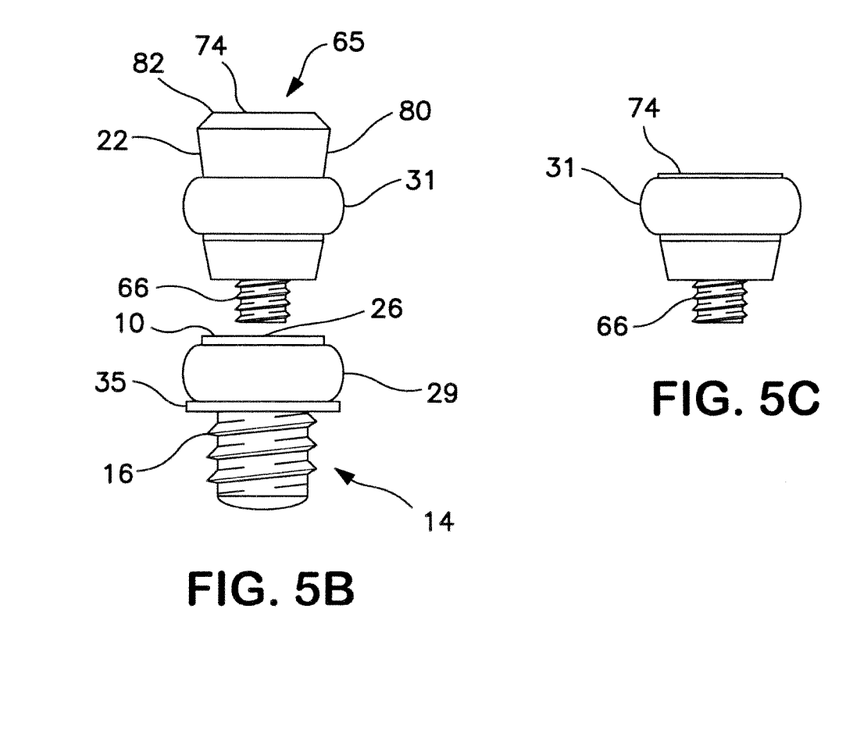
Figure 5D:
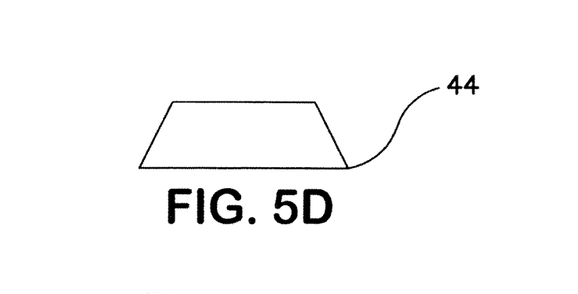
FIG. 5D is a side view of one embodiment of the inventive osteointegrative portion consistent with the present invention.

In another embodiment of the invention, as shown in FIG. 5B, the stage II assembly 65 may have an osteointegrative portion 31 with a shape, configuration or other features that allow for optimal integration and physical stability of the implant with the bone during bone growth, in a manner discussed above with regard to the osteointegrative portion.

The osteotropic/angiotropic material stabilizer 46, as shown in FIG. 1 may in some cases be removed and replaced with an osteotropic/angiotropic material stabilizer 45 similar to the one shown in FIG. 6B. The osteotropic/angiotropic material stabilizer 45 has several openings, each 56. As previously discussed these openings 56 may increase the stabilization of additional osteotropic/angiotropic material to permit vascular ingrowth and/or serve as a region through which bone may form.

The stage II assembly 64, as shown in FIG. 2F, may have, for example, a threaded bore 72 on the coronal end 74 of the stage II assembly into which a stage II cover screw 76, shown in FIG. 2G, may be threaded. The stage II assembly 64 also has a tool engagement surface such as a slot 78 to allow attachment of the stage II assembly 64 to the stage I assembly 14.

The coronal end 74 of the stage II assembly 65, as shown in FIGS. 5A and 5B may have a polished collar 80, and an angled finish line 82. The angled finish line 82 has properties similar to those discussed with regard to angled finish line 25.

Figure 1B:
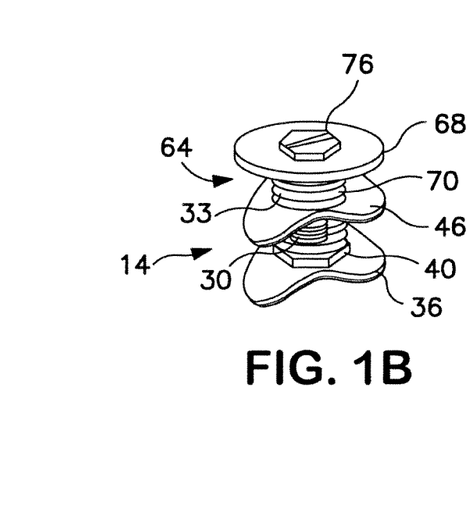
FIG. 1B is a perspective view of one embodiment of the inventive staged implant system.
Figures 4A, 4B, 4C:
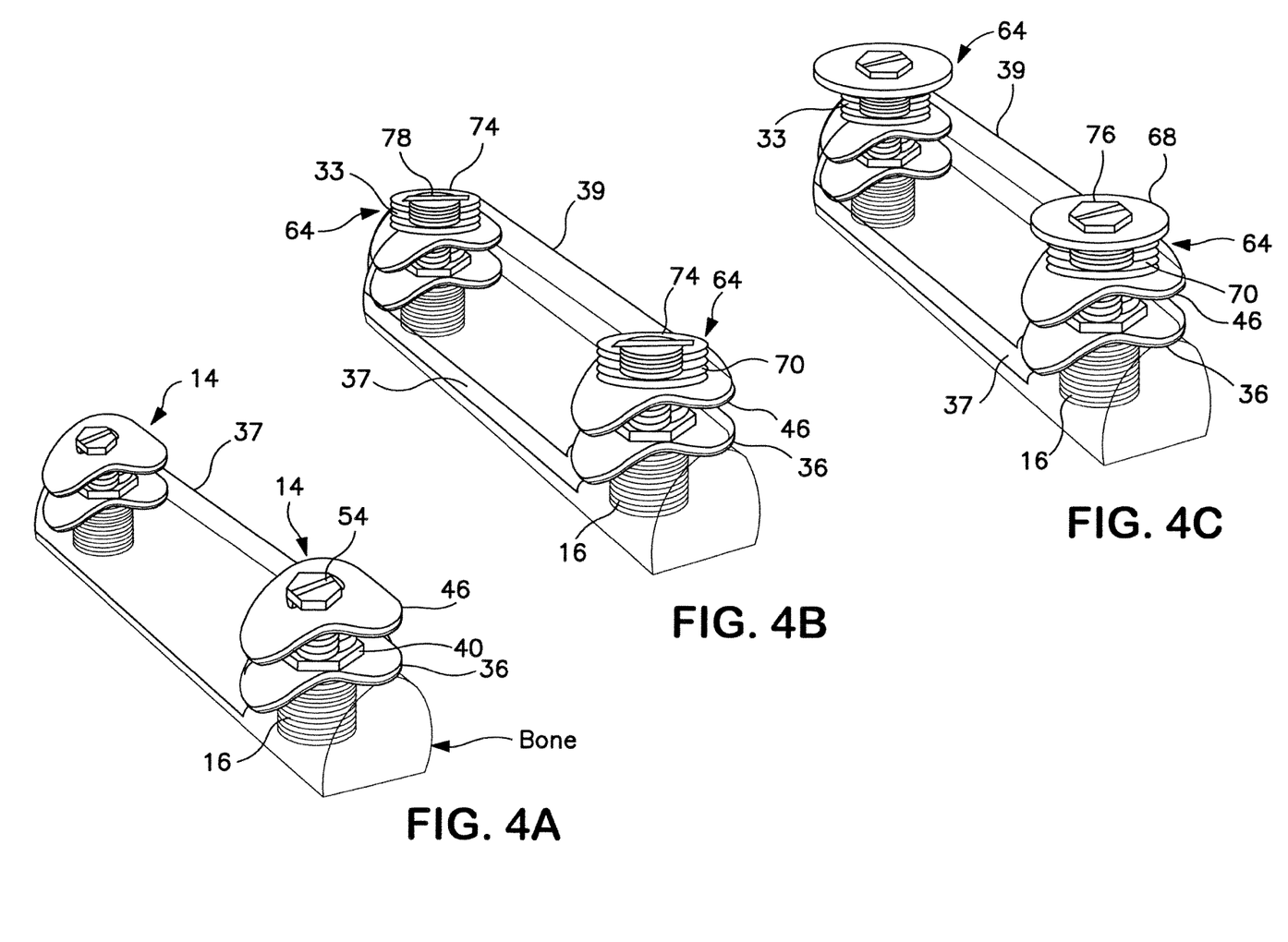
FIGS. 4A-4C are perspective views illustrating examples of some inventive staged implants with osteotropic/angiogenic materials embedded in bone during stage II surgery process.

A stage II osteotropic/angiotropic material stabilizer 68, as illustratively shown in FIGS. 1B, 2G and 4C may be present in the stage II assembly 64. The stage II osteotropic/angiotropic material stabilizer 68 may have a generally planar shape and be comprised of a material that lessens and/or prevents cellular adhesion. The stage II osteotropic/angiotropic material stabilizer 68 has an opening 84, illustratively shown in FIG. 1A. The stage II osteotropic/angiotropic material stabilizer 68 may be retained to the coronal end 74 of the stage II assembly 64 by a stage II cover screw 76 that is engaged within the threaded bore 72. Alternatively, as shown in FIGS. 6C and 6D, the stage II osteotropic/angiotropic material stabilizer 68 may be integral with the cover screw.

In another embodiment of the invention, as illustratively shown in FIG. 6C, the stage II osteotropic/angiotropic material stabilizer 69 may fit over and around the polished collar 82 of coronal end 74. Additional osteotropic/angiotropic material (not shown) may be placed in association with stage II assembly 65 and retained in place by the stage II osteotropic/angiotropic material stabilizer 69 in a manner similar to that shown in FIG. 4C where additional osteotropic/angiotropic material 39 is placed in association with stage II assembly 64 and retained in place by stage II osteotropic/angiotropic material stabilizer 68, to further enhance bone growth.

In another embodiment, for example as shown in FIGS. 3C and 4C, multiple stage I and/or stage II implant assemblies are utilized adjacent to one another. In this embodiment additional bracing or splinting elements, similar to those shown in FIG. 7 may be attached from one implant to the next implant to stabilize or further support the implants. This bracing provides added positional stability for the adjacent implants and/or osteotropic/angiotropic material securement.

The material used for the stage I assembly and the stage II assembly is chosen for with respect to known biocompatibility as implant material and is guided by well-known principals of osseointegration, implant design, and characterization of biomechanical properties. As an illustrative example, materials such as titanium, titanium alloys, steel, steel alloys, cobalt alloys, nickel alloys, metal composites, ceramics, glasses, biologically derived materials, natural polymers and synthetic polymers may be used alone or in combination throughout the invention. Furthermore, the structural implant and components can be made from any of the resorbable and/or non-resorbable materials well known in the art. When the components are made predominantly from a non-resorbable material such as titanium or titanium alloy, the structural implant would remain in place for prosthetic restoration.

The present invention encompasses a method of promoting the growth of new bone tissue with or without the use of autogenous or non-autogenous graft materials. In one embodiment, with illustrative reference to FIGS. 2A-2G and 3A-3C, a section of bone (not shown in FIGS. 2A-2G) is surgically exposed or accessed and the anchoring component 18 is fastened into the bone to the level of the preliminary stabilizer 36 by engaging a tool (not shown) with the tool engagement surface 28. The implant may then be fastened, for example, to a depth of about 4 mm to about 6 mm into the bone. This depth, it should be understood, may be based on the location of the preliminary stabilizer 35 if fixed to the initial implant portion 16 or on the location where a separate preliminary stabilizer 36 will be placed. A preliminary stabilizer 36, if a separate component, may then be placed over the exposed portion of the initial implant portion 16. During placement the preliminary stabilizer 16 may be threaded onto, or may pass freely over, the exposed portion of the implant. The preliminary stabilizer 36 may then be secured against the bone by tightening the preliminary stabilizer nut 40. Osteotropic/angiotropic material 32 may then be placed over the implant. The osteotropic/angiotropic material 32 may also be punched through with the transmucosal portion 22 of the implant, or otherwise associated with the implant. The osteotropic/angiotropic material 32 is then secured in place with an osteotropic/angiotropic material stabilizer 46.

Where bone augmentation is desired over a greater area, multiple implants may be used. FIG. 3 illustrates the use of multiple implants with osteotropic/angiotropic materials during a stage I surgery. Naturally more than two implants may be used in combination. When multiple implants are used, the implants are secured into bone adjacent to one another. This allows new bone growth to be obtained in any number of configurations. For example, the implants may be arranged in a substantially linear pattern or over a circular, or otherwise shaped, area.

As illustratively shown in FIG. 3B, osteotropic/angiotropic material 37 may be associated with multiple stage I assemblies 14. For example, the osteotropic/angiotropic material 37 forms an extended structure which can be installed over the coronal ends 10. The osteotropic/angiotropic material 37 may then be secured in place, as shown in FIG. 3C, when the osteotropic/angiotropic material stabilizer 46 and is secured with the closure screw 54 fastened into the coronal end 10 of the implant. In the case of a stage II assembly 64 as shown in FIG. 4B osteotropic/angiotropic material 39 may be placed over the coronal ends 74 of two or more stage II assemblies. As shown in FIG. 4C the osteotropic/angiotropic 39 material may then be secured in place with the osteotropic/angiotropic material stabilizers 68 and secured with closure screws 76 fastened into the coronal end 51 of the implant. Placement of the osteotropic/angiotropic material 37 and/or osteotropic/angiotropic material 39 between multiple implants, as discussed above, may increase retention and stabilization of the osteotropic/angiotropic material. For example, the osteotropic/angiotropic material may be supported and retained physically at each end by the inserts.

In another embodiment of the invention, as illustratively shown in FIGS. 7A-7D bracing or splinting materials, such as mesh 60 and plate 62 can be associated with the multiple implants. This additional bracing or splinting may connect the implants to further stabilize or support the implants in the bone. This bracing also may function to provide additional positional stability for the osteotropic/angiotropic material (not shown). The implant structure and associated osteotropic/angiotropic material may then be covered with a membrane, similar to membrane 58 as previously discussed with regard to FIG. 3B, that acts as a barrier to the in-growth of epithelial cells and connective tissue fibroblasts into the osteotropic/angiotropic material.

The implant site is then closed with, for example, a primary flap closure using techniques well known in the surgical arts. For instance, in the event that insufficient tissue is present to close the implant site, special surgical techniques previously described or additional material may be used. Such additional material can be any material well known in the medical art including autologous, allologous and/or engineered tissue grafts, natural and/or fabrics, and polymers.

The quantity and quality of bone growth at the implant site is determined after a period of time. This determination may be accomplished either remotely via radiograph or Dual Energy X-ray Absorptiometry (DEXA) scan or through direct observation.

With reference to FIG. 3C, after three to six months the site can be reopened and cover screw 54 and osteotropic/angiotropic material stabilizer 46 removed. The bone is then observed and the bone growth is determined. If bone growth is adequate, a transmucosal prosthetic segment (not shown) may then be attached to the implant. The prosthetic connector attachment may utilize, for example, adhesive bonding or mechanical attachment such as on screw-retained abutments well known in the medical arts.

If additional bone is needed, an additional stage, for example, a stage II assembly 64 is fastened, as shown in FIG. 1, with the engagement portion 66 to the connecting portion, such as threaded bore 26 of the initial implant portion 16. This fastening can be aided through engagement of a tool (not shown) with the tool engagement surface 78. FIGS. 4A-4C illustratively show progressive installation of stage II assemblies (each 64) to implanted stage I assemblies (each 14) as well as the incorporation of osteotropic/angiotropic material 37 and osteotropic/angiotropic material 39. After stage II assembly 64 placement and maturation of new calcified tissues around the stage II assembly, the assembled implant composed of the stage I assembly 14 and the stage II assembly 64 may be supported and retained by, for example, approximately 8 mm or more of bone height and be ready for the attachment of the prosthetic segment (not shown).

Experimental use of one embodiment of the invention included use of the osteotropic/angiotropic material in the form of a bone allograft scaffold. The osteotropic/angiotropic material was used in conjunction with an implant having an osteointegrative portion with a roughened titanium surface, an implant having an osteointegrative portion with an alkaline surface, and an implant having an osteointegrative portion with a calcium phosphate surface. Vertical bone growth was achieved in a range of between 1.67 mm to 2.29 mm for the implant with a roughened titanium surface; in a range of between 1.79 mm to 2.15 mm for the implant with the alkaline surface; and in a range of between 2.09 mm to 2.89 mm for the implant with the calcium phosphate surface.

It should be understood that while preferred embodiments of the foregoing invention have been set forth for purposes of illustration, the foregoing description should not be deemed a limitation of the invention herein. Accordingly, various modifications, adaptations and alternatives may occur to one skilled in the art without departing from the spirit and scope of the present invention.

What is claimed is:

1. An implant for promoting the growth of new vertical bone beyond existing bone level, comprising:
   an initial implant portion having at its apical end a fastening means for directly embedding into direct contact with existing bone and having a coronal end that is configured to be proximal to existing bone level;
   an osteointegrative portion disposed at the coronal end of the initial implant portion and which is configured to be substantially situated beyond the existing bone level, wherein said osteointegrative portion further comprises an osteotropic/angiotropic material disposed thereon; and
   an osteotropic/angiotropic stabilizer disposed at the coronal end of the osteointegrative portion and which prevents movement of the osteotropic/angiotropic material; and
   a preliminary stabilizer disposed generally at the coronal end of the initial implant portion for providing lateral and/or retentive stability to the initial implant portion during and/or after growth of new bone on the implant;
   wherein said implant promotes the growth of new vertical bone along the osteointegrative portion beyond the existing bone level.

2. The implant of claim 1, wherein the osteoptropic/angiotropic stabilizer prevents the movement of the osteotropic/angiotropic material by exerting pressure on said material.

3. The implant of claim 1, wherein the preliminary stabilizer extends laterally outwardly from the outermost surface of the initial implant portion.

4. The implant of claim 1, wherein the preliminary stabilizer contacts a countersunk area in the preexisting bone adjacent the coronal end of the initial implant portion.

5. The implant of claim 1, wherein the preliminary stabilizer is configured to be disposed at the existing bone level.

6. The implant of claim 1, wherein the preliminary stabilizer is an integral part of the initial implant portion.

7. The implant of claim 1, wherein the osteotropic/angiotropic material is a resorbable organic material, a resorbable inorganic material, or a non-resorbable material.

8. The implant of claim 1, wherein the osteotropic/angiotropic material is a scaffold material selected from the group consisting of one or more of autogenous bone, bone allograft, synthetic polymers, natural polymers, ceramics and composite materials.

9. The implant of claim 8, wherein the scaffold material is resorbable.

10. The implant of claim 8, wherein the scaffold material has surfaces and conduits for one or more of retention, stabilization, controlled release and/or bioavailability modulation of osteoactive compounds.

11. The implant of claim 8, wherein the scaffold material comprises a barrier membrane.

12. The implant of claim 11, wherein the barrier membrane is resorbable.

13. The implant of claim 11, wherein the barrier membrane is non-resorbable.

14. The implant of claim 11, wherein the barrier membrane is polytetrafluoroethylene or collagen.

15. The implant of claim 1, wherein the osteotropic/angiotropic material is a scaffold material further comprising at least one of bone morphogenetic protein (BMP) and vascular endothelial growth factor (VEGF).

16. The implant of claim 1, wherein the osteotropic/angiotropic material is a resorbable collagen comprising at least one of bone morphogenetic protein (BMP) and vascular endothelial growth factor (VEGF).

17. The implant of claim 1, wherein the osteotropic/angiotropic stabilizer is curved or arcuate in shape.

18. The implant of claim 1, wherein the osteotropic/angiotropic stabilizer comprises one or more cutouts or protrusions for enhancing stabilization, cell growth or vascularization of the osteotropic/angiotropic material.

19. The implant of claim 1, wherein the osteotropic/angiotropic stabilizer comprises a threaded opening to engage threads on the coronal end of the osteointegrative portion.

20. The implant of claim 1, wherein the osteotropic/angiotropic stabilizer is engaged with the coronal end of the osteointegrative portion by a screw.

21. The implant of claim 20, wherein the osteotropic/angiotropic stabilizer is integral with the screw.

22. The implant of claim 1, wherein the fastening means of the initial implant are screw threads.

23. The implant of claim 1, further comprising a transmucosal portion disposed coronal to the osteointegrative portion.

24. A method of promoting the growth of new vertical bone beyond existing bone level without the use of bone grafts, comprising:
   embedding an implant comprising:
      (i) an initial implant portion having at its apical end a fastening means for directly embedding into direct contact with existing bone and having a coronal end that is configured to be proximal to existing bone level;
      (ii) an osteointegrative portion disposed at the coronal end of the initial implant portion and which is configured to be substantially situated beyond the existing bone level, wherein said osteointegrative portion further comprises an osteotropic/angiotropic material disposed thereon;
      (iii) an osteotropic/angiotropic stabilizer disposed at the coronal end of the osteointegrative portion and which prevents movement of the osteotropic/angiotropic material; and
      (iv) a preliminary stabilizer disposed generally at the coronal end of the initial implant portion for providing lateral and/or retentive stability to the initial implant portion during and/or after growth of new bone on the implant;
   allowing passage of a period of time sufficient to result in the growth of new vertical bone beyond the existing bone level along the osteointegrative portion.

25. The method of claim 24, wherein the initial implant portion of the implant is configured to be embedded to about 4 to 6 mm into the existing bone.

26. The method of claim 24, further comprising disposing an additional bracing or splinting material onto the implant.

27. The method of claim 24, further comprising surgically closing the implant site after embedding the implant.

28. The method of claim 24, wherein the quantity and quality of the bone growth is determined after a period of time.

29. The method of claim 24, wherein the quantity and quality of the bone growth are determined by radiograph, dual energy X-ray absorptiometry (DEXA).

30. The method of claim 24, further comprising covering the embedded implant with a membrane that functions as a barrier to the in-growth of epithelial cells and connective tissue fibroblasts into the osteotropic/angiotropic material.

* * * * *